United States Patent [19]

Siczek et al.

[11] Patent Number: 4,955,046
[45] Date of Patent: Sep. 4, 1990

[54] C-ARM FOR X-RAY DIAGNOSTIC EXAMINATION

[76] Inventors: Aldona A. Siczek; Bernard W. Siczek, both of 1252 Chinook Way, Boulder, Colo. 80303

[21] Appl. No.: 338,945

[22] Filed: Apr. 17, 1989

[51] Int. Cl.$^5$ ............................................. H05G 1/02
[52] U.S. Cl. .................................. 378/197; 378/198
[58] Field of Search ............................ 378/195–198

[56] References Cited

U.S. PATENT DOCUMENTS

| 2,168,209 | 8/1939 | Haupt | 378/197 |
|---|---|---|---|
| 3,803,417 | 4/1974 | Kok | 378/196 |
| 4,150,297 | 4/1979 | Borggren | 378/197 |
| 4,209,706 | 6/1980 | Nunan | 378/197 |
| 4,481,656 | 11/1984 | Janssen et al. | 378/196 |
| 4,868,845 | 9/1989 | Koropp | 378/197 |
| 4,887,287 | 12/1989 | Cobben | 378/197 |
| 4,918,716 | 4/1990 | Hahn | 378/197 |

FOREIGN PATENT DOCUMENTS

| 0235834 | 9/1987 | European Pat. Off. | 378/198 |
|---|---|---|---|
| 2238706 | 2/1974 | Fed. Rep. of Germany | 378/196 |
| 2248015 | 4/1974 | Fed. Rep. of Germany | 378/197 |

Primary Examiner—Craig E. Church

[57] ABSTRACT

A C-arm X-ray diagnostic equipment is disclosed which C-arm provides: an increased range of orbital rotation; a longer range of vertical travel of C-arm from low to high vertical positions; safer counter balanced vertical movement; the horizontal axis of rotation drawn through the isocenter of the C-arm for a multiple of X-ray beam projections without repositioning of the patient being imaged; remotely controlled passive locking arrangement for securing the C-arm firmly in any necessary position for safety; remotely controlled C-arm positioning.

A novel non-uniform curvature of C-arm where the inner outline is other than semicircular is selected for structural strength.

13 Claims, 6 Drawing Sheets

C-ARM FOR X-RAY DIAGNOSTIC EXAMINATION

FIELD OF INVENTION

This invention relates to a C-arm X-ray diagnostic equipment, and, more particularly, relates to a mobile C-arm and a ceiling suspended C-arm for effecting C-arm positioning.

BACKGROUND OF INVENTION

The use of a C-arm X-ray diagnostic equipment in a diagnostic examination and/or surgical procedures is well known, and such C-arms have herefore been controlled utilizing various constructions and various devices for effecting needed movements.

Improvements in C-arms are, however, deemed to be useful and/or needed for at least some applications. In particular, now known C-arms have failed to provide adequate imaging coverage of a patient undergoing surgical or cardiac procedures and, more particularly, have not been able to impart sufficient range of orbital and vertical movements of the C-arm for effective use and have required repositioning of the patient being imaged in order to obtain a multiple of X-ray beam projections.

SUMMARY OF THE INVENTION

This invention provides an improved C-arm for use in a diagnostic examination and/or medical treatments allowing the C-arm to be displaced in orbital direction in an increased range, to have a horizontal axis of rotation close to the isocenter of the C-arm and lower in respect to the floor level, to be moved vertically in a larger range and yet to be positioned lower relative to the floor level.

It is therefore an object of this invention to provide an improved C-arm useful in diagnostic examinations and cardiac and surgical procedures.

It is another object of this invention to provide an improved C-arm which provides adequate range of orbital movement of C-arm, and, thus adequate coverage of the patient in the cross table examination.

It is still another object of this invention to provide an improved C-arm with an enhanced range of vertical travel of the C-arm from low to high.

It is still another object of this invention to provide an improved C-arm with the center of rotation around the horizontal axis coinciding with the isocenter in order to be able to set a multiple of X-ray beam projections without repositioning the patient being imaged.

It is still another object of this invention to provide an improved C-arm which enables the C-arm to be operated manually and/or remotely utilizing various devices and controls for effecting needed movement.

It is yet another object of this invention to provide a novel passive locking arrangements for securing the C-arm firmly in any necessary position.

DETAILED DESCRIPTION OF THE PRESENTLY PREFERRED EMBODIMENT

The description of this invention is illustrated in relation to a mobile C-arm. In another preferred embodiment this invention relates to a ceiling suspended C-arm.

Figure 1:
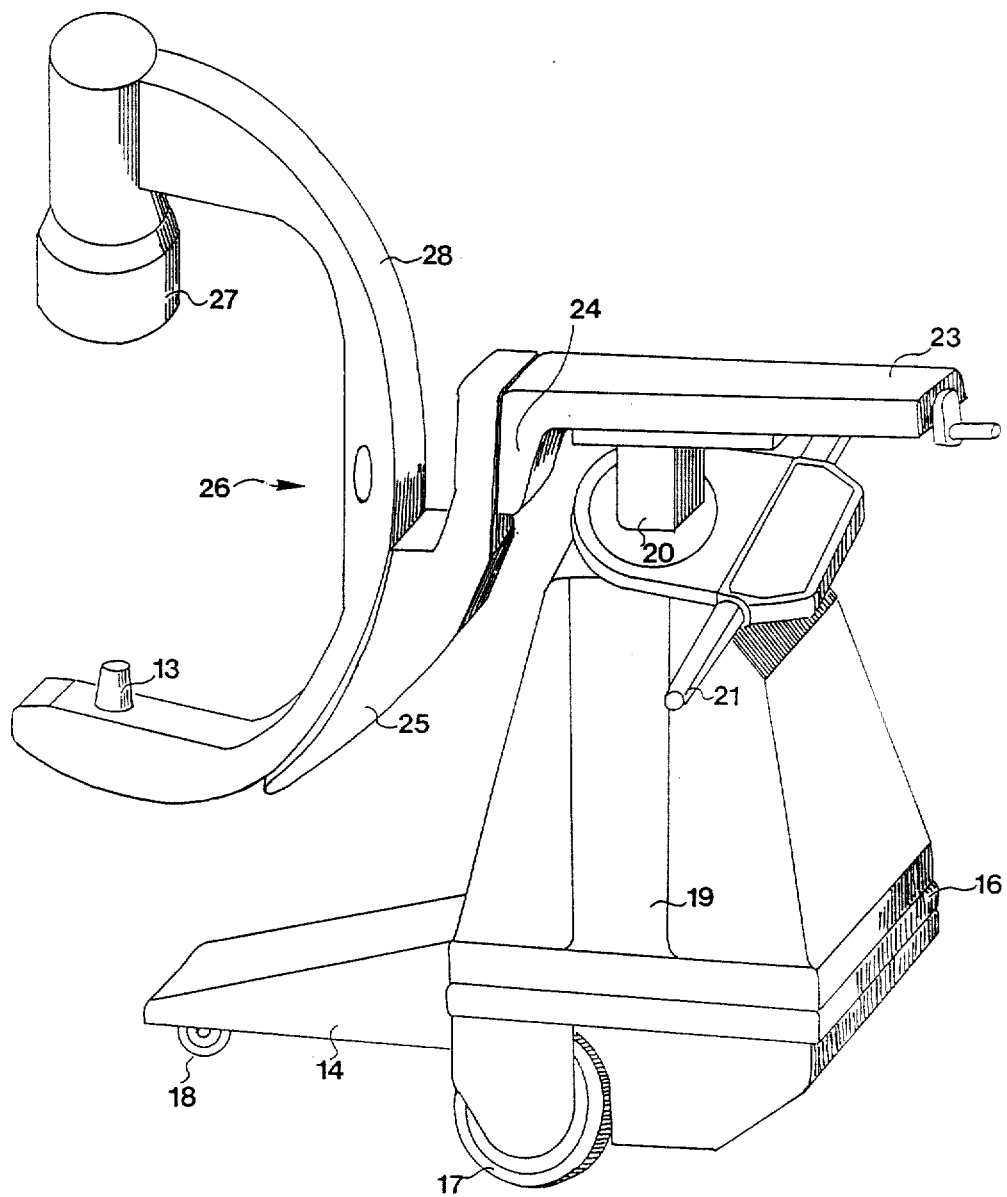
FIG. 1 shows an isometric view of the mobile C-arm equipment of the invention.
Figure 2:
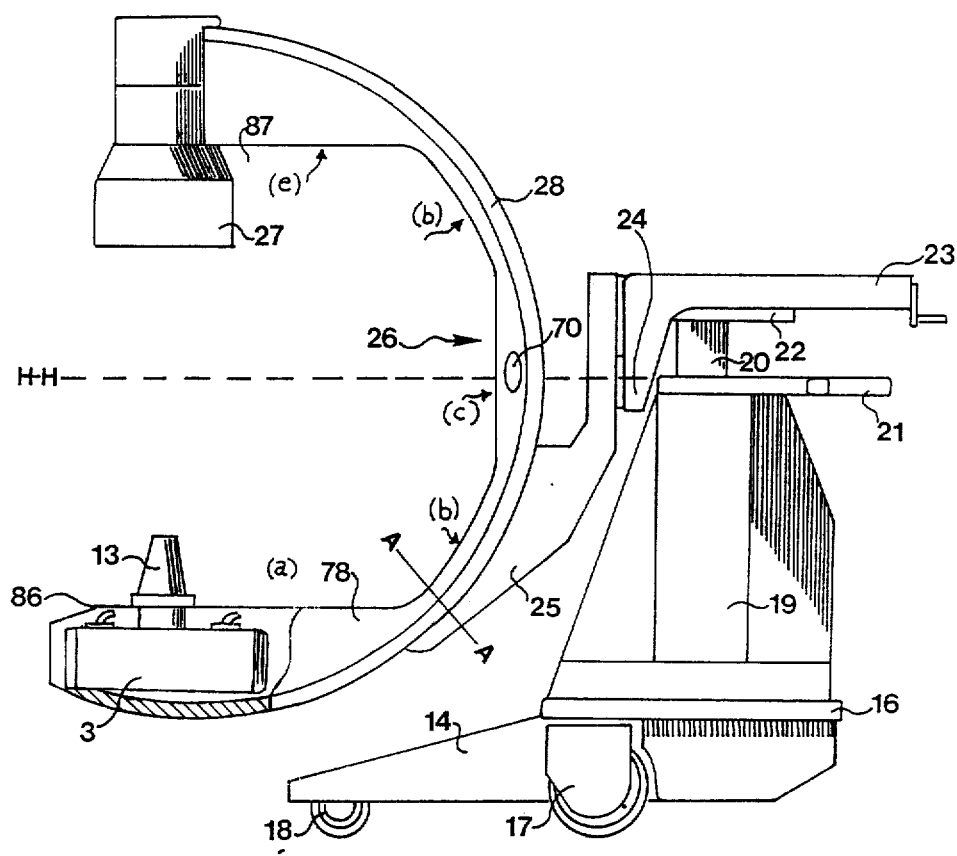
FIG. 2 shows a side view of the mobile C-arm equipment.

Mobile C-arm diagnostic equipment according to this invention is best known by the isometric drawing of FIG. 1, augmented by the side view of FIG. 2. As shown, mobile C-arm includes a base means 16, having mounted thereon a vertically extending support structure 19; a vertically movable column 20, which column extends upwardly from structure 19 (as shown best in FIG. 3); a structure 23, which structure extends horizontally and has a downwardly extending section 24 and is moveably mounted on a support plate 22 (which plate 22 is mounted on the top of column 20) for a lengthwise movement and a swivel rotation around vertical axis; an L-arm 25 rotateably mounted on section 24 for circular rotation around horizontal axis H—H (as shown best in FIG. 4); a C-arm 26 moveably mounted on L-arm 25 for orbital rotation (as shown best in FIG. 6).

C-arm 26 includes an arc-shaped structure 28 (having an outline as brought out more fully herein- after), an image receptor 27, such as an image intensifier (as shown) or a film cassette or the like, mounted on structure 28 at one end and an X-ray collimator 13 mounted at the opposite end and disposed directly on the top of an X-ray tube 3 which tube is disposed inside arc-shaped structure 28, wherein the isocenter of said structure coincides with axis H—H.

Base means 16 is supported on two big wheels 17 controlled by a handle 21 and disposed intermediate the inside edge of base means 16 and the inside edge of a support member 14 which support member extends horizontally from said base for stability and includes a small swivel wheel 18.

Figure 3:
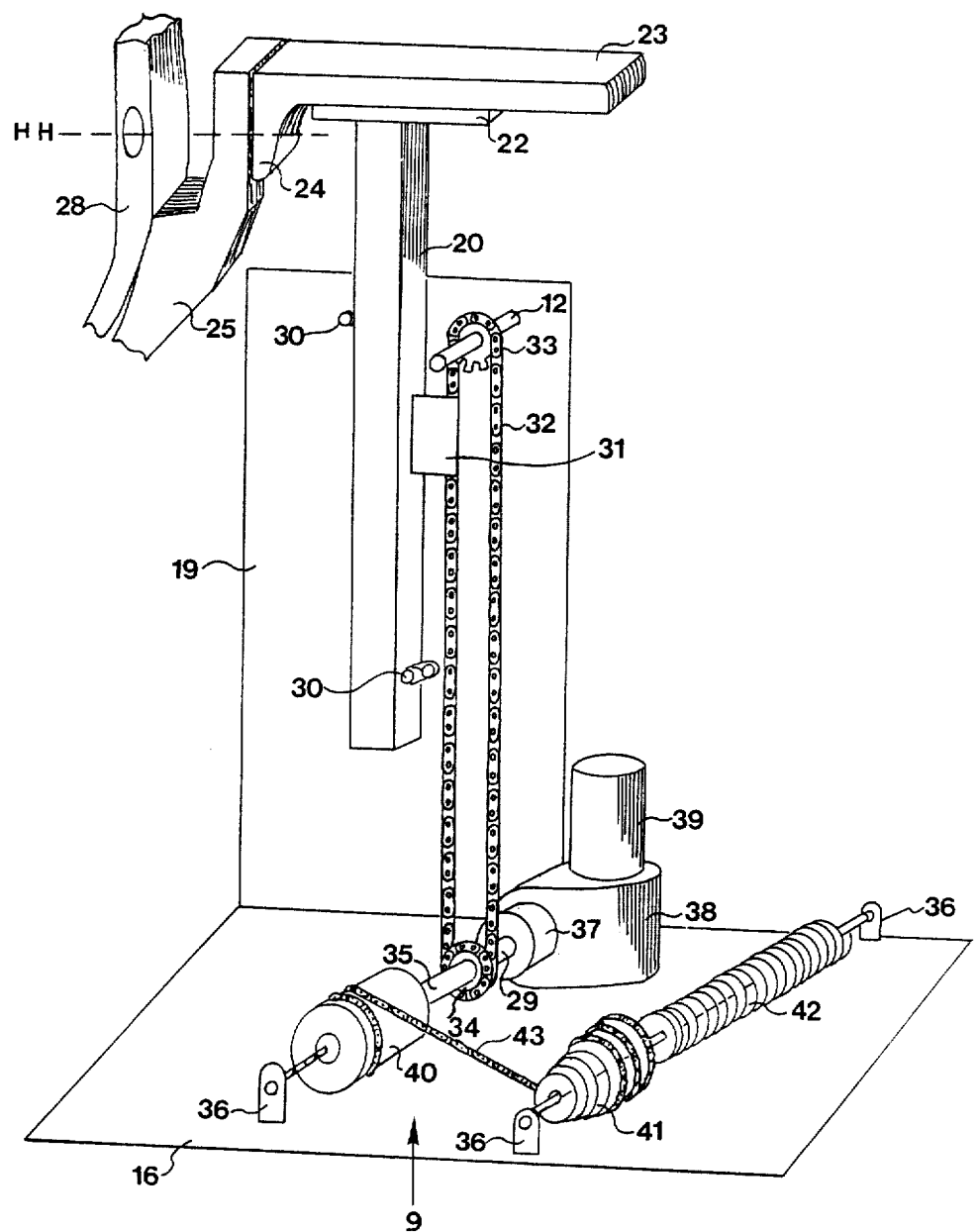
FIG. 3 shows details of the drive means for the vertically extendable column that supports the C-arm.

FIG. 3 illustrates a drive means for the vertical movement of column 20 which drive means includes a chain 32 connected by means of a plate-like attachment 31 to column 20, which column is guided by rollers 30. Chain 32 extends around upper and lower sprockets 33 and 34. Upper sprocket 33 is mounted on a pin 12 which is affixed to structure 19. Lower sprocket 34 is mounted on a shaft 35, which shaft is freely rotateable within a bearing support 36 which support is affixed to base means 16. An electric motor 39 is mounted on base means 16 and has a worm gear reducer 38 with an output drive shaft 29 engageable with shaft 35 by means of a clutch 37 so that driving rotation of the motor causes movement of the column. Worm gear reducer 38 further acts as a passive locking arrangement for securing column 20 firmly in any necessary position.

To counter balance the weight of C-arm during vertical movement a first counter balancing means 9 is provided which means comprises: a cable drum 40 mounted on shaft 35, a conical cable drum 41 connected to a torsion spring 42; drum 41 and torsion spring 42 mounted on a shaft 44, which shaft is rotateably supported at opposite ends on bearing supports 36 which supports are affixed to base means 16; a cable 43 having one end secured to one drum and the other end secured to the other drum and extending therebetween so that the rotation of drum 40 causes the rotation of drum 41 and, further, so that torsion spring 42 stores the rotation energy when column 20 is being lowered and releases that stored energy when column 20 is being raised.

Figure 4:
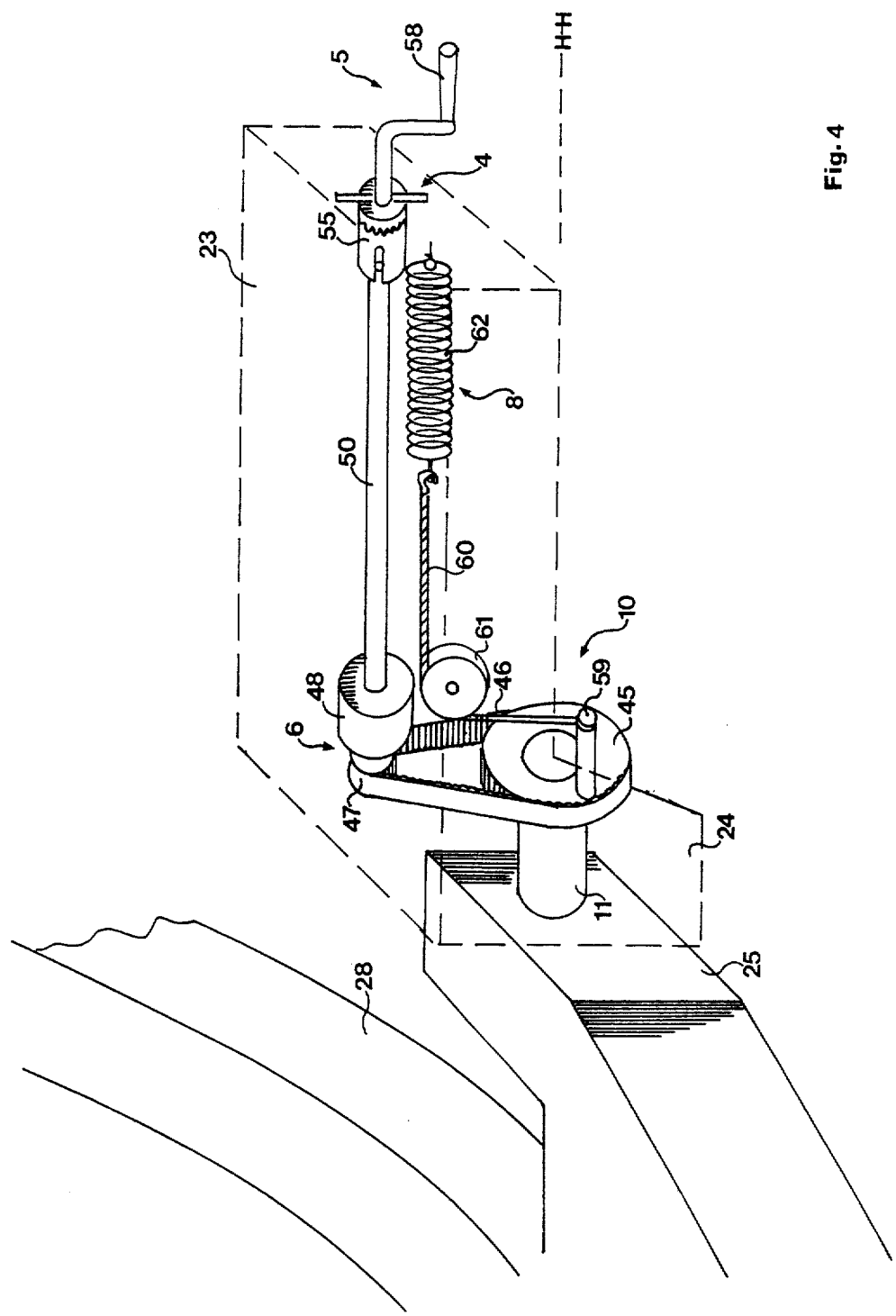
FIG. 4 shows details of the drive means for rotating the L shaped C-arm support.

FIG. 4 illustrates a drive means for the horizontal rotation of L-arm 25 around axis H—H, which drive means includes a motion transmitting means 10, which means 10 transmit driving rotation from a first shaft to a second shaft wherein said second shaft is disposed lower than the first shaft in respect to floor level. Means 10 further reduces torque of this driving rotation.

As shown in FIG. 4 transmitting motion means comprises a freely rotateable shaft 11 mounted on portion 24 of structure 23. Shaft 11 has mounted L-arm 25 on one end and a timing pulley 45 on the opposite end. A freely rotateable shaft 50 extending lengthwise through the center of structure 23 is mounted at opposite ends on structure 23 by means of bearing mounts (not shown). A smaller timing pulley 47 and a clutch 48 are mounted on one end of a shaft 50 in close proximity of each other. A timing belt 46 extends around timing pulleys 45 and 47. A drive imparting means 5, such as a hand crank 58 (as shown) or an electric motor or the like, is mounted on the opposite end of shaft 50 to impart driving rotation of said shaft. A rotation control means 4, such as pins 57 immobilizing hand crank 58 (as shown) or a mechanical brake or the like, which means precludes rotation of shaft 11 to secure firmly C-arm 26 in any necessary position. Hand crank 58 is mounted by a means of a hub 55, which hub allows said crank when moved inwardly to rotate freely causing rotation of C-arm 26.

While the rotation of C-arm may be effected by rotation control means 4 (such as pins 57) which preclude rotation of shaft 50 as needed, such rotation may also be effected by controlling energization of a clutch engaging means 6.

Clutch engaging means 6, or a passive lock, retains clutch 48 engaged by spring action for imparting driving motion to L-arm 25 while not engaged and causes said clutch to become disengaged while said means are energized.

To achieve a counter balanced rotation of the L-arm and C-arm a second counter balancing means 8 is provided which means 8 comprises a tension spring 62 affixed to structure 23 at one end and the opposite end to a bolt 59, which bolt is mounted on pulley 45 by means of a cable 60 guided by a roller 61. While C-arm is being rotated, the spring tension varies so that to counter balance the weight of the C-arm 26.

Figure 5:
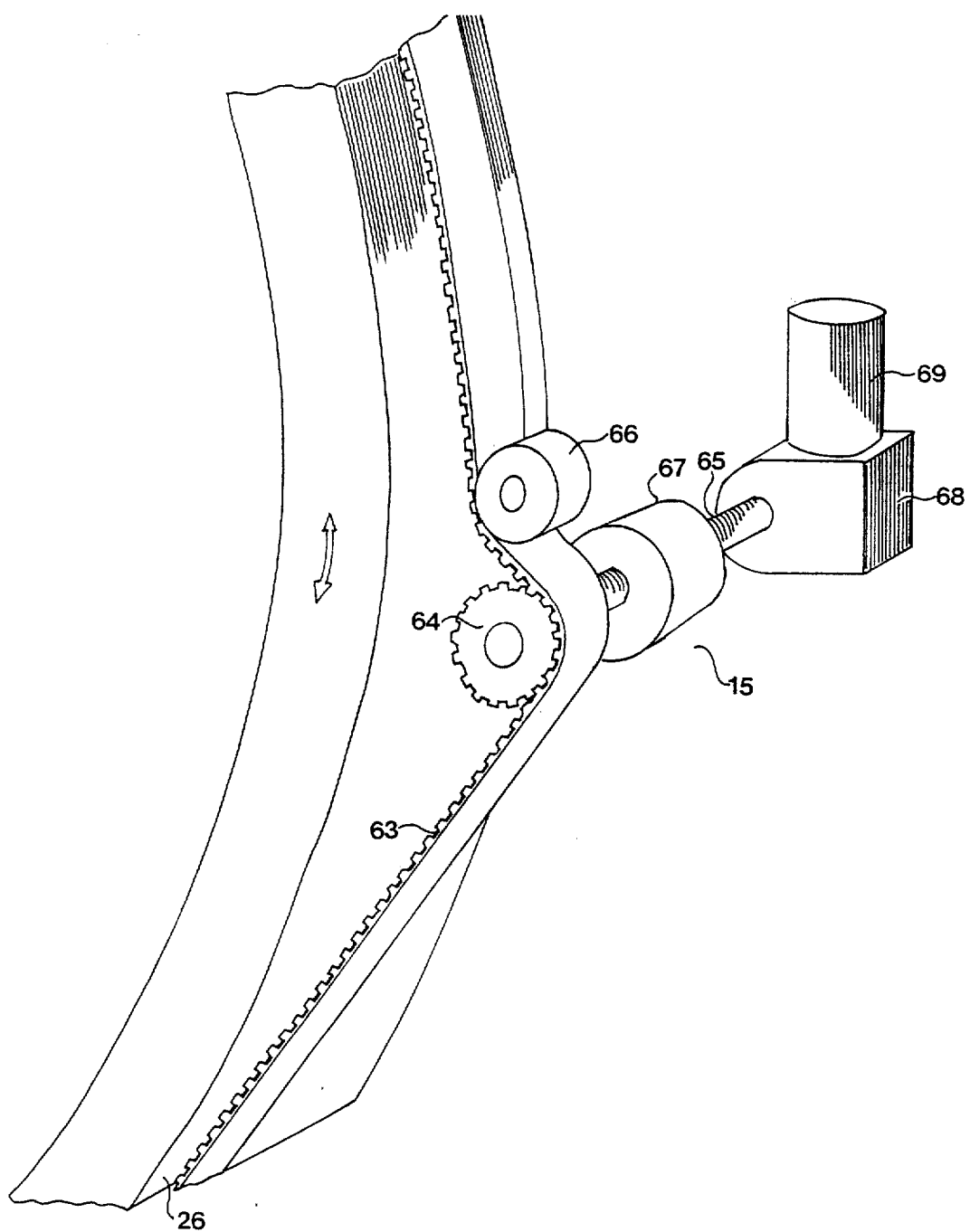
FIG. 5 shows details of the drive means for orbital rotation of the C-arm.

FIG. 5 illustrates a drive means 15 for orbital arc movement which drive means comprises: an electric motor 69, a gear reducer 68, a drive shaft 65 extending from said reducer and having a clutch 67 and a timing pulley 64 mounted thereon in close proximity of each other, a timing belt 63 extending along the outside circumference of arc 26 and over pulley 64 and mounted on the opposite ends of arc 26 and being tensioned by a roller 66. The orbital rotation of C-arm is accomplished by energizing motor 69 so that driving rotation of shaft 65 causes orbital rotation of C-arm 26.

While the orbital movement of C-arm may be affected by controlling energization of electric motor 69, such movement may also be effected by controlling energization of clutch engaging means 7, or a passive lock. Clutch engaging means 7 retains clutch 67 engaged by spring action for imparting orbital rotation to C-arm 26 while not energized and causes said clutch to become disenqaged while energized.

Figure 6:
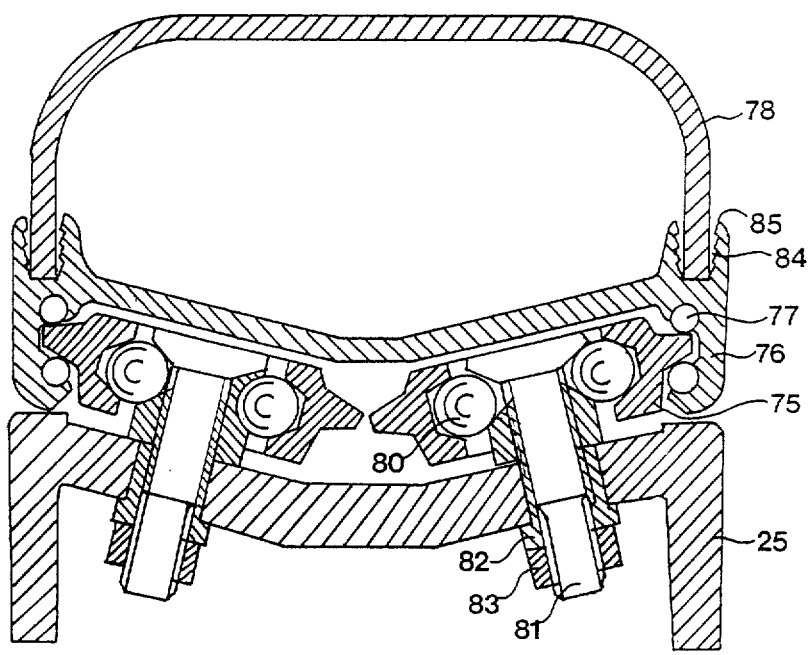
FIG. 6 shows a cross section of the C-arm through line A—A of FIG. 2.

FIG. 6 is a cross section view taken through line A—A of FIG. 3 illustrating arc-shaped structure 28 utilized in conjunction with the orbital movement of C-arm 26.

Arc-shaped structure 28 comprises an inside member 78 and an outside member 76 which outside member includes two pairs of hard steel inserts 77 embodied on opposite sided thereof. Inserts 77 roll on two pairs of wedge-shaped rings 75 (shown one pair) which rings constitute outside rings of four-point bearings 80 mounted on a bearing axle 81, which axle is mounted on L-arm 25 by means of a offset bushing 82 with a bolt 83, which bushing allows for preloading of the bearings.

A non-uniform inner curvature of inner member 78 where the inner outline being other than semi-circular in shape as best shown in FIG. 2 is selected to enhance the structural strength and utility of the C-arm. This curvature being a horizontal line at opposite ends (a) and (e) and being transferred to an arc line in sections (b) and (d) and having the central portion (c) wider to compensate for a cable outlet 70 weakening the structure therein. A cover 86 for X-ray tube 3 with an opening for collimator 13 and a cover 87 for a portion of image receptor 27 constitute end portions of C-arm 26 for strength and esthetics.

Outer member 76 extends at one end under X-ray tube 3 and at the opposite end over a portion of image receptor 27 to increase the range of orbital movement of C-arm.

Outer member 76 is joined with inner member 78 using an adhesive; outer member 76 may be made from an extruded aluminum; inner member 78 may be made from a composite material, preferably carbon fiber, or fabricated aluminum. Outer member 76 has channels 84 with grooves 85 wherein inner member 78 is substantially inserted for stronger binding.

In another embodiment of this invention outer member 76 and inner member 78 are joined by means of at least one additional member on each side for structural strength when larger dimensions are needed.

What is claimed is:

1. A C-arm X-ray apparatus for use in diagnostic examinations comprising: a C-arm being an arc-shaped member having an image source and an image receptor mounted on opposite ends thereof, a vertical structure for supporting said C-arm, wherein said structure is moveably mounted on a base means and connected to a drive means for vertical displacement, a counter-balancing means for a vertical movement comprising a torsion spring connected to a first drum, said torsion spring and said first drum mounted on a first shaft secured on opposite ends to said base means, a second drum mounted on a second shaft secured to said base means and connected to said first drive means and further coupled to said first drum so that the rotation of said second drum causes the rotation of said first drum and further causes said torsion spring to store the rotation energy while the C-arm is being lowered and to release that stored energy when said C-arm is being raised.

2. A C-arm X-ray apparatus for use in diagnostic examinations comprising: a C-arm being an arc-shaped member having an image source and an image receptor mounted on opposite ends thereof, a horizontal structure mounted on a base means and including a downwardly extending section, which section has an arm support rotateably mounted thereon for supporting said C-arm, said arm support being connected with a motion transmitting means for transmitting motion of a drive means, which drive means comprises:
- a first freely rotateable shaft extending lengthwise through said horizontal structure and mounted thereon, said shaft connected with a drive imparting means,
- a second freely rotateable shaft mounted on said downwardly extending section,
- a motion transmitting means to transmit motion and reduce torque from said first shaft to said second shaft for rotation of said arm around an axis of said second shaft, wherein said axis is disposed lower with respect to the floor level than said horizontal structure.

3. The system of claim 2 wherein said drive imparting means includes a hand crank means and a rotation control means which means preclude rotation of said hand crank means as desired.

4. The system of claim 2 wherein said drive imparting means includes an electric motor and a rotation control means to preclude rotation of said first shaft as desired.

5. A C-arm X-ray apparatus for use in diagnostic examinations comprising: a C-arm being an arc shaped structure having an image source and an image receptor mounted on opposite ends thereof, an arm member for supporting said C-arm, wherein said arm member is rotateably mounted on a support means and connected with a drive means for rotation around a horizontal axis, which drive means includes a clutch and a clutch engaging means for retaining said clutch engaged by spring action while not energized and causing said clutch to become disengaged while engaged.

6. A C-arm X-ray apparatus for use in diagnostic examinations comprising; a C-arm being an arc shaped structure having an image source and an image receptor mounted on opposite ends thereof, said C-arm orbitally supported by an arm member and including a drive means for producing an orbital displacement of said C-arm relative to said arm member, wherein said drive means includes a clutch and a clutch engaging means for retaining said clutch engaged while not energized and causing said clutch to become disengaged while energized.

7. A C-arm X-ray apparatus for use in diagnostic examinations, said apparatus including a C-arm for carrying an X-ray source and an image receptor, said C-arm comprising an inner circumference and an outer circumference, wherein a first member forms said inner circumference and a second member forms said outer circumference and further, said first member and said second member are joined together with an adhesive.

8. The system of claim 7 wherein said members are joined by means of other members.

9. The system of claim 7 wherein one of said member has channels and said other member is inserted therein.

10. The system of claim 9 wherein said channels have grooves.

11. The system of claim 7 wherein said outer member has two inserts made of a hard metal and embodied therein on each side thereof.

12. The system of claim 11 wherein said inserts roll on wedge shaped rings which rings constitute outside rings of bearings.

13. The system of claim 12 wherein a distance between said bearings is adjustable by an offset bushing.

* * * * *